(12) United States Patent
Lee

(10) Patent No.: US 8,277,851 B2
(45) Date of Patent: Oct. 2, 2012

(54) HERBAL MEDICINAL COMPOSITION AND HERBAL MEDICINAL EXTRACT FOR INDUCING PRODUCTION OF PERIPHERAL BLOOD STEM CELLS AND METHOD FOR PREPARING THE SAME

(76) Inventor: Chen-Yu Lee, Taipei (TW)

( * ) Notice: Subject to any disclaimer, the term of this patent is extended or adjusted under 35 U.S.C. 154(b) by 210 days.

(21) Appl. No.: 12/923,847

(22) Filed: Oct. 12, 2010

(65) Prior Publication Data

US 2011/0111050 A1    May 12, 2011

(30) Foreign Application Priority Data

Nov. 20, 2009 (TW) .............................. 98138360 A

(51) Int. Cl.
*A61K 36/00* (2006.01)
*A61K 36/54* (2006.01)
*A61K 36/65* (2006.01)
*A61K 36/236* (2006.01)
*A61K 36/725* (2006.01)
*A61K 36/258* (2006.01)
*A61K 36/539* (2006.01)
*A61K 36/232* (2006.01)
*A61K 36/481* (2006.01)

(52) U.S. Cl. ........ 424/725; 424/739; 424/757; 424/756; 424/728

(58) Field of Classification Search .................. None
See application file for complete search history.

*Primary Examiner* — Qiuwen Mi
(74) *Attorney, Agent, or Firm* — Bacon & Thomas, PLLC

(57) ABSTRACT

A herbal medicinal composition and a herbal medicinal extract for inducing production of peripheral blood stem cells and a method for preparing the same. The herbal medicinal composition contains herbal medicinal herbs disclosed herein such as Cinnamomum Ramulus, Paeoniae (Ovatae) Radix Rubra, Glycyrrhizae Radix, Zingiberis Rhizoma, Jujubae Fructus, Anelicae Radix, and Astragali Radix.

12 Claims, 2 Drawing Sheets

HERBAL MEDICINAL COMPOSITION AND HERBAL MEDICINAL EXTRACT FOR INDUCING PRODUCTION OF PERIPHERAL BLOOD STEM CELLS AND METHOD FOR PREPARING THE SAME

BACKGROUND OF THE INVENTION

1. Field of the Invention

The present invention relates to a herbal medicinal composition and a herbal medicinal extract, and a method for preparing the same and, more particularly, a herbal medicinal composition and a herbal medicinal extract for inducing production of peripheral blood stem cells and a method for preparing the same.

2. Description of Related Art

Medicinal science has found that stem cells can travel to tissues of human bodies where apoptosis, inflammation, atrophy owing to injury, aging, or necrosis occurs, and that is, finding a new home. In these tissues, stem cells can self-differentiate, develop the tissue, restore necrosis, atrophy, and apoptosis, or attack, inhibit, transform benign and malignant cells with abnormal proliferation. Among various stem cells, hematopoietic stem cells (HSCs) are capable of mobilizing from bone marrow to peripheral blood for self-renewal. In other words, at least one of the daughter cells from hematopoietic progenitor cell division has to maintain the characteristics of the mother cell (the undivided hematopoietic progenitor cell), i.e. keeping undifferentiated and being capable of continuous cell division. In addition, the daughter cells can differentiate into various specific blood cells. Hence, in human bodies, HSCs are the fastest cell in division and differentiation and considerably active to complement aging or injured cells everyday so as to keep physiology in the normal balance.

In general, HSCs locate in bone marrow of human bodies, and the number thereof is approximately one percent of total lymphocytes therein. Only a few HSCs will mobilize from bone marrow to peripheral blood, and the number thereof is approximately 0.1 percent of total lymphocytes. However, it is currently reported that HSCs will mobilize from bone marrow to peripheral blood during an increase in the number of leukocytes after the human bodies are subjected to chemotherapy at a high dose. Otherwise, injection of granulocyte colony-stimulating factor (G-CSF), a kind of leukocyte growth factor, will stimulate HSCs, and it also can achieve mobilization.

With progress of technology day by day, various malignant cancers are treated by a combination of surgery, radiotherapy, and chemotherapy. Nevertheless, a dose used in radiotherapy or chemotherapy usually has to be limited to prevent injury to the bone marrow of the patient, and thus the efficacy of the therapy also reduces owing to the limited dose. Therefore, some researchers suggest autograft of HSCs. That is, healthy HSCs are aspirated from the actual patient, stored for a while, and then grafted into the patient after radiotherapy or chemotherapy at a high dose so as to restore the hematopoietic function of the bone marrow which is inhibited or injured thereafter.

Based on the ways of obtaining HSCs, autograft techniques are classified into a bone marrow transplant and a peripheral blood stem cells (PBSCs) transplant. The bone marrow transplant is to directly aspirate bone marrow out of a patient and then proceed with a transplant. The PBSCs transplant is to stimulate HSCs to mobilize to peripheral blood, where HSCs used to locate at an extremely low level, so as to obtain PBSCs by cell isolation, and then proceed with a transplant.

Notwithstanding, because aspiration of bone marrow requires hospitalization and general anaesthesia during surgery, there may be drawbacks such as anesthesia risk, infection, cardio-cerebrovascular or pulmo-renovascular infarction, and post-operation pain (POP). By contrast, aspiration of PBSCs has none of the drawbacks mentioned above, but since injection of G-CSF is required to stimulate mobilization, there may be bone, waist, and chest pain, osteoporosis, lower than average number of platelets, abnormal proliferation of leucocytes to 50-100 thousand (even to several hundred thousand), a possible increase in proliferation of cancer stem cells and abnormal cells to result in a new cancer, relapse of a treated cancer, and risks such as pneumonia, hepatitis, splenomegaly, hemorrhage, rash, illness, or even shock.

Hence, if a related drug able to stimulate mobilization of stem cells can be developed without the risks and symptoms after injection of G-CSF mentioned above, it is more advantageous to PBSC transplant and self-restore of aging or injured cells in human bodies.

SUMMARY OF THE INVENTION

The object of the present invention is to provide a herbal medicinal composition, a herbal medicinal extract, and a method for preparing the same so as to induce production of peripheral blood stem cells and also increase the number of CD34(+) cells in peripheral blood lymphocytes to achieve hematopoiesis.

To achieve the object, an aspect of the present invention provides a herbal medicinal composition for inducing production of peripheral blood stem cells or increasing the number of CD34(+) cells in peripheral blood lymphocytes. The herbal medicinal composition includes the following herbal medicinal herbs: Cinnamomum Ramulus (*Cinnamomum cassia* Presl.), Paeoniae (Ovatae) Radix Rubra (*Paeonia veitchii* Lynch.), Glycyrrhizae Radix (*Glycyrrhiza uralensis* Fischer et DC), Zingiberis Rhizoma (*Zingiber officinale* Roscoe), Jujubae Fructus (*Zingiber officinale* Mill.), Ginseng Radix (*Panax ginseng* C. A. MEYER), Deer Antler (*Elaphurus davidianus* Milne-Edwards), Scutellariae Radix (*Scutellaria baicalensis* Georgi), Anelicae Radix (*Angelica sinensis* Diels), and Astragali Radix (*Astragalus membranaceus* Bunge).

Another aspect of the present invention provides a method of preparing a herbal medicinal extract for inducing production of peripheral blood stem cells or increasing the number of CD34(+) cells in peripheral blood lymphocytes. The method includes the following steps: mixing a herbal medicinal composition comprising the following herbal medicinal herbs: Cinnamomum Ramulus, Paeoniae (Ovatae) Radix Rubra, Glycyrrhizae Radix, Zingiberis Rhizoma, Jujubae Fructus, Scutellariae Radix, Anelicae Radix, and Astragali Radix; heating the herbal medicinal composition with water to form an extract; and adding Ginseng Radix and Deer Antler into the extract.

Further another aspect of the present invention provides a herbal medicinal extract for inducing production of peripheral blood stem cells or increasing the number of CD34(+) cells in peripheral blood lymphocytes. The herbal medicinal extract is prepared by the abovementioned method.

In the herbal medicinal composition, the herbal medicinal extract, and the method for preparing the same, the Cinnamomum Ramulus is comprised in an amount from 2.5 to 10 parts by weight, Paeoniae (Ovatae) Radix Rubra is comprised in an amount from 2.5 to 10 parts by weight, Glycyrrhizae Radix is comprised in an amount from 2.5 to 10 parts by weight, Zingiberis Rhizoma is comprised in an amount from 2.5 to 10 parts by weight, Jujubae Fructus is comprised in an amount from 2.5 to 10 parts by weight, Ginseng Radix is comprised in an amount from 1.5 to 6 parts by weight, Deer Antler is comprised in an amount from 0.5 to 2 parts by weight, Scutellariae Radix is comprised in an amount from 1.5 to 6 parts by weight, Anelicae Radix is comprised in an amount from 1 to 4 parts by weight, and Astragali Radix is comprised in an amount from 5 to 20 parts by weight. Preferably, the Cinnamomum Ramulus is comprised in an amount from 3.75 to 7.5 parts by weight, Paeoniae (Ovatae) Radix Rubra is comprised in an amount from 3.75 to 7.5 parts by weight, Glycyrrhizae Radix is comprised in an amount from 3.75 to 7.5 parts by weight, Zingiberis Rhizoma is comprised in an amount from 3.75 to 7.5 parts by weight, Jujubae Fructus is comprised in an amount from 3.75 to 7.5 parts by weight, Ginseng Radix is comprised in an amount from 2.25 to 4.5 parts by weight, Deer Antler is comprised in an amount from 1 to 1.5 parts by weight, Scutellariae Radix is comprised in an amount from 2.25 to 4.5 parts by weight, Anelicae Radix is comprised in an amount from 1.5 to 3 parts by weight, and Astragali Radix is comprised in an amount from 7.5 to 15 parts by weight.

Besides, in the herbal medicinal composition, the herbal medicinal extract, and the method for preparing the same, the time and temperature of the heating to water, the amount of the water added, and the weight ratio of the original water to the final water after heating all are not particularly limited. Preferably, the heating is to heat the water to 80-100° C. for 60-90 minutes; the water is used in an amount of 5-15 times the weight of the herbal medicinal composition; and the extract is evaporated by heating until liquid of the extract reaches a half to a quarter the weight of the water.

DETAILED DESCRIPTION OF THE PREFERRED EMBODIMENT

Example

Cinnamomum Ramulus (18.5 g), Paeoniae (Ovatae) Radix Rubra (18.5 g), Glycyrrhizae Radix (18.5 g), Zingiberis Rhizoma (18.5 g), Jujubae Fructus (18.5 g), Scutellariae Radix (11.25 g), Anelicae Radix (7.5 g), and Astragali Radix (37.5 g) were cut into slices, respectively. The abovementioned herbal medicinal herbs were heated with water (1200 g) to 90° C. or more for 60-90 minutes until the liquid of the resultant extract remaining had been reduced to about 400 g. The resultant extract was filtrated to remove the herb residue. Ginseng Radix (11.25 g) and Deer Antler (3.75 g) were powdered and then added in the filtrated extract to form a herbal medicinal extract.

Comparative Example

Cinnamomi ramulus (18.5 g), Paeoniae (Ovatae) Radix Rubra (18.5 g), Glycyrrhizae Radix (18.5 g), green Zingiberis Rhizoma (18.5 g), Jujubae Fructus (18.5 g), Anelicae Radix (7.5 g), and Astragali Radix (37.5 g) were cut into slices, respectively. The abovementioned herbal medicinal herbs were heated with water (1200 g) to 90° C. or more for 60-90 minutes until the liquid of the resultant extract remaining was reduced to about 400 g. The resultant extract was filtrated to remove the herb residue.

Experimental Example

Subjects A, B, and C (three persons) were orally administered with the extract of Comparative Example twice a day, every morning and night, for two weeks. The blood of the subjects A, B, and C was drawn. Peripheral blood lymphocytes were isolated from the blood of the subjects A, B, and C by the known method in the art, and counted by a flow cytometry to measure ratios of CD34(+), CD184(+), and CD133(+) cells. This administration was Time 1.

In next two weeks, the subjects A, B, and C were orally administered with the extract of Example in the manner same as described above. Then, ratios of CD34(+), CD184(+), and CD133(+) cells were measured from the blood of the subjects A, B, and C. This administration was Time 2.

In further next two weeks, the administered drug was changed back to the extract of Comparative Example, and taken by the subjects A, B, and C in the same manner as described above. Then, ratios of CD34(+), CD184(+), and CD133(+) cells were measured from the blood. This administration was Time 3.

In final two weeks, the administered drug was changed into the extract of Example, and taken by the subjects A, B, and C in the manner same as described above. Then, ratios of CD34 (+), CD184(+), and CD133(+) cells were measured from the blood. This administration was Time 4.

There has been a report showing that CD34 and CD133 both are cell markers of HSCs. Although not all of the cells expressing CD34 and CD 133 are HSCs, this identification is a means to find HSCs in the current research. Therefore, isolation of peripheral blood lymphocytes from blood to measure the number of the cells expressing CD34 and CD133 (i.e., CD34(+) and CD133(+) cells) is a preliminary method for speculating the number of HSCs in peripheral blood, i.e. PBSCs.

Figure 1:
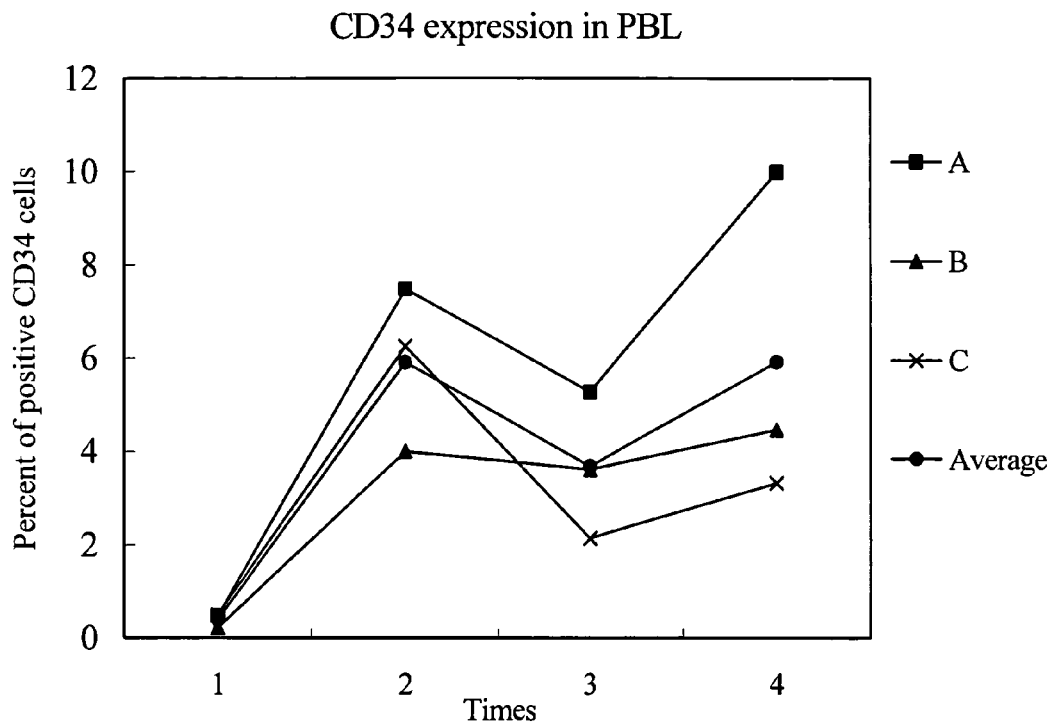
FIG. 1 is a curve showing the percent of positive CD34 cells in peripheral blood lymphocytes.

FIG. 1 is a curve showing the percent of positive CD34 cells (CD34(+) cells) in peripheral blood lymphocytes. Time 1 of FIG. 1 shows that the percent of CD34(+) cells is low (Comparative Example). However, once the extract of Comparative Example was changed into that of Example, Time 2 of FIG. 1 shows the percent of CD34(+) cells increases remarkably in the drawn blood of the subjects A, B, and C. Once the administered drug was changed back to the extract of Comparative Example, Time 3 of FIG. 1 shows that the percent of CD34(+) cells decreases considerably. Finally, once the administered drug was changed into the extract of Example, Time 4 of FIG. 1 shows the percent of CD34(+) cells significantly rises again.

Figure 2:
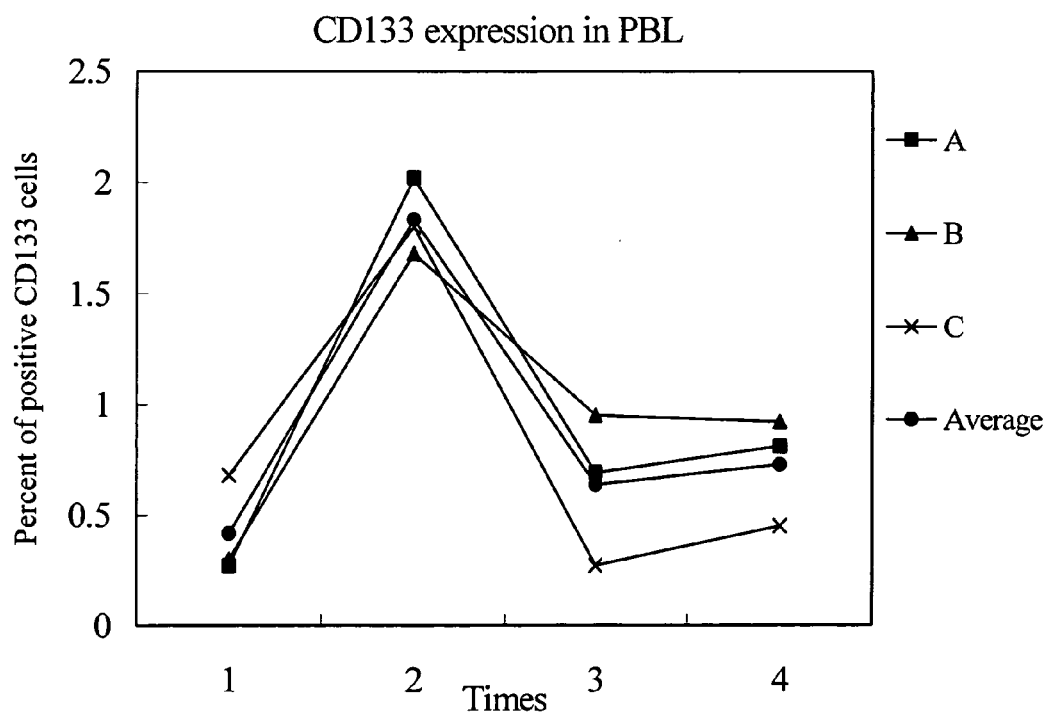
FIG. 2 is a curve showing the percent of positive CD133 cells in peripheral blood lymphocytes.

FIG. 2 is a curve showing the percent of positive CD133 cells (CD133(+) cells) in peripheral blood lymphocytes. Time 1 of FIG. 2 shows that the percent of CD133(+) cells is low (Comparative Example). However, once the extract of Comparative Example was changed into that of Example, Time 2 of FIG. 2 shows the percent of CD133(+) cells increases remarkably. Once the administered drug was changed back to the extract of Comparative Example, Time 3 of FIG. 2 shows that the percent of CD133(+) cells decreases considerably. Finally, once the administered drug was changed into the extract of Example, Time 4 of FIG. 2 shows the percent of CD133(+) cells significantly rises again.

Figure 3:
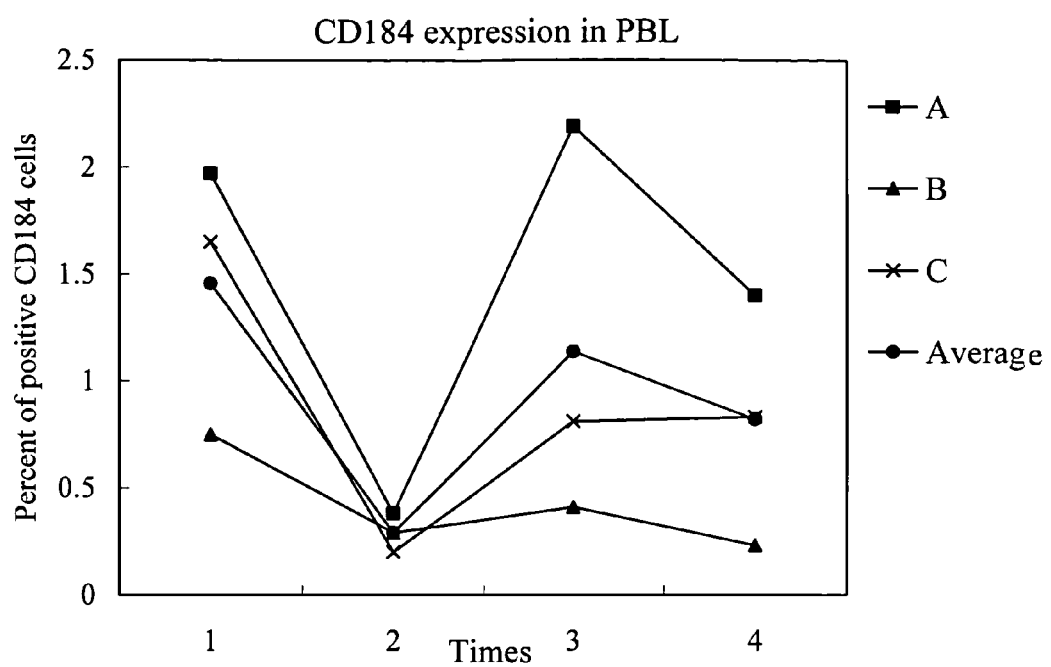
FIG. 3 is a curve showing the percent of positive CD184 cells in peripheral blood lymphocytes.

FIG. 3 is a curve showing the percent of positive CD184 cells (CD184(+) cells) in peripheral blood lymphocytes. Time 1 of FIG. 3 shows that the percent of CD184(+) cells is high (Comparative Example), unlike CD34 in Time 1 of FIG. 1 and CD133 in that of FIG. 2. However, once the extract of Comparative Example was changed into that of Example, Time 2 of FIG. 2 shows the percent of CD184(+) cells decreases remarkably. Once the administered drug was changed back to the extract of Comparative Example, Time 3 of FIG. 3 shows that the percent of CD133(+) cells increases considerably. Finally, once the administered drug was changed into the extract of Example, Time 4 of FIG. 3 shows the percent of CD184(+) cells significantly descends again. Since there is a report showing that CD184 relates to the homing of the stem cells, the result of CD184 is contrary to those of CD34 and CD133.

It is observed that the percent of CD34(+) and CD133(+) cells increases and that of CD184(+) cells decreases in the peripheral blood lymphocytes isolated from the blood of the subjects. Accordingly, administration of the herbal medicinal composition of the present invention can induce the increase of the HSCs in the peripheral blood, i.e. PBSCs.

Although the present invention has been explained in relation to its preferred embodiment, it is to be understood that many other possible modifications and variations can be made without departing from the scope of the invention as hereinafter claimed.

What is claimed is:

1. A herbal medicinal composition for inducing production of peripheral blood stem cells, said composition comprising the following herbal medicinal herbs: Cinnamomum Ramulus in an amount from 2.5 to 10 parts by weight, Paeoniae Radix Rubra in an amount from 2.5 to 10 parts by weight, Glycyrrhizae Radix in an amount from 2.5 to 10 parts by weight, Zingiberis Rhizoma in an amount from 2.5 to 10 parts by weight, Jujubae Fructus in an amount from 2.5 to 10 parts by weight, Ginseng Radix in an amount from 1.5 to 6 parts by weight, Deer Antler in an amount from 0.5 to 2 parts by weight, Scutellariae Radix in an amount from 1.5 to 6 parts by weight, Angelicae Radix in an amount from 1 to 4 parts by weight, and Astragali Radix in an amount from 5 to 20 parts by weight.

2. The herbal medicinal composition as claimed in claim 1, wherein the Cinnamomum Ramulus is comprised in an amount from 3.75 to 7.5 parts by weight, the Paeoniae Radix Rubra is comprised in an amount from 3.75 to 7.5 parts by weight, the Glycyrrhizae Radix is comprised in an amount from 3.75 to 7.5 parts by weight, the Zingiberis Rhizoma is comprised in an amount from 3.75 to 7.5 parts by weight, the Jujubae Fructus is comprised in an amount from 3.75 to 7.5 parts by weight, the Ginseng Radix is comprised in an amount from 2.25 to 4.5 parts by weight, the Deer Antler is comprised in an amount from 1 to 1.5 parts by weight, the Scutellariae Radix is comprised in an amount from 2.25 to 4.5 parts by weight, the Angelicae Radix is comprised in an amount from 1.5 to 3 parts by weight, and the Astragali Radix is comprised in an amount from 7.5 to 15 parts by weight.

3. A herbal medicinal extract for inducing production of peripheral blood stem cells, said extract is prepared by the following steps:
mixing a herbal medicinal composition comprises the following herbal medicinal herbs: Cinnamomum Ramulus in an amount from 2.5 to 10 parts by weight, Paeoniae Radix Rubra in an amount from 2.5 to 10 parts by weight, Glycyrrhizae Radix in an amount from 2.5 to 10 parts by weight, Zingiberis Rhizoma in an amount from 2.5 to 10 parts by weight, Jujubae Fructus in an amount from 2.5 to 10 parts by weight, Scutellariae Radix in an amount from 1.5 to 6 parts by weight, Angelicae Radix in an amount from 1 to 4 parts by weight, and Astragali Radix in an amount from 5 to 20 parts by weight;
heating the herbal medicinal composition with water to form an extract;
and adding Ginseng Radix in an amount from 1.5 to 6 parts by weight and Deer Antler in an amount from 0.5 to 2 parts by weight into the extract.

4. The herbal medicinal extract as claimed in claim 3, wherein the Cinnamomum Ramulus is comprised in an amount from 3.75 to 7.5 parts by weight, the Paeoniae Radix Rubra is comprised in an amount from 3.75 to 7.5 parts by weight, the Glycyrrhizae Radix is comprised in an amount from 3.75 to 7.5 parts by weight, the Zingiberis Rhizoma is comprised in an amount from 3.75 to 7.5 parts by weight, the Jujubae Fructus is comprised in an amount from 3.75 to 7.5 parts by weight, the Ginseng Radix is comprised in an amount from 2.25 to 4.5 parts by weight, the Deer Antler is comprised in an amount from 1 to 1.5 parts by weight, the Scutellariae Radix is comprised in an amount from 2.25 to 4.5 parts by weight, the Angelicae Radix is comprised in an amount from 1.5 to 3 parts by weight, and the Astragali Radix is comprised in an amount from 7.5 to 15 parts by weight.

5. The herbal medicinal extract as claimed in claim 4, wherein the heating step comprises heating the water to 90-100° C. for 60-90 minutes.

6. The herbal medicinal extract as claimed in claim 5, wherein the water is used in an amount of 5-15 times the weight of the herbal medicinal composition.

7. The herbal medicinal extract as claimed in claim 6, wherein the extract is evaporated by heating until the volume of the extract is reduce to a quarter to a half of the original volume.

8. A method of preparing a herbal medicinal extract for inducing production of peripheral blood stem cells, said method comprising the following steps:
mixing a herbal medicinal composition comprising the following herbal medicinal herbs: Cinnamomum Ramulus in an amount from 2.5 to 10 parts by weight, Paeoniae Radix Rubra in an amount from 2.5 to 10 parts by weight, Glycyrrhizae Radix in an amount from 2.5 to 10 parts by weight, Zingiberis Rhizoma in an amount from 2.5 to 10 parts by weight, Jujubae Fructus in an amount from 2.5 to 10 parts by weight, Scutellariae Radix in an amount from 1.5 to 6 parts by weight, Angelicae Radix in an amount from 1 to 4 parts by weight, and Astragali Radix in an amount from 5 to 20 parts by weight;
heating the herbal medicinal composition with water to form an extract;
and adding Ginseng Radix in an amount from 1.5 to 6 parts by weight and Deer Antler in an amount from 0.5 to 2 parts by weight into the extract.

9. The method as claimed in claim 8, wherein the Cinnamomum Ramulus is comprised in an amount from 3.75 to 7.5 parts by weight, the Paeoniae Radix Rubra is comprised in an amount from 3.75 to 7.5 parts by weight, the Glycyrrhizae Radix is comprised in an amount from 3.75 to 7.5 parts by weight, the Zingiberis Rhizoma is comprised in an amount from 3.75 to 7.5 parts by weight, the Jujubae Fructus is comprised in an amount from 3.75 to 7.5 parts by weight, the Ginseng Radix is comprised in an amount from 2.25 to 4.5 parts by weight, the Deer Antler is comprised in an amount from 1 to 1.5 parts by weight, the Scutellariae Radix is comprised in an amount from 2.25 to 4.5 parts by weight, the Angelicae Radix is comprised in an amount from 1.5 to 3 parts by weight, and the Astragali Radix is comprised in an amount from 7.5 to 15 parts by weight.

10. The method as claimed in claim 9, wherein the heating step comprises heating the water to 90-100° C. for 60-90 minutes.

11. The method as claimed in claim 10, wherein the water is used in an amount of 5-15 times the weight of the herbal medicinal composition.

12. The method as claimed in claim 11, wherein the extract is evaporated by heating until the volume of the extract is reduced to a quarter to a half of the original volume.

* * * * *

UNITED STATES PATENT AND TRADEMARK OFFICE
Certificate

Patent No. 8,277,851 B2                                                                                   Patented: October 2, 2012

On petition requesting issuance of a certificate for correction of inventorship pursuant to 35 U.S.C. 256, it has been found that the above identified patent, through error and without any deceptive intent, improperly sets forth the inventorship.
   Accordingly, it is hereby certified that the correct inventorship of this patent is: Chen-Yu Lee, Taipei (TW); Hsin-I Ma, New Taipei City (TW); Hsiu-Mei Hsieh, Taipei City (TW); and Hsiu-Chin Ho, New Taipei City (TW).

Signed and Sealed this Twenty-fourth Day of September 2013.

*TERRY A. MCKELVEY*
*Supervisory Patent Examiner*
*Art Unit 1655*
*Technology Center 1600*